(12) United States Patent
Liggett et al.

(10) Patent No.: US 12,257,248 B2
(45) Date of Patent: Mar. 25, 2025

(54) BRONCHODILATORS FOR TREATING OBSTRUCTIVE LUNG DISEASE

(71) Applicants: University of South Florida, Tampa, FL (US); Rutgers, The State University of New Jersey, New Brunswick, NJ (US)

(72) Inventors: Stephen Liggett, Tampa, FL (US); James Leahy, Tampa, FL (US); Donghwa Kim, Tampa, FL (US); Steven An, Highland Park, NJ (US)

(73) Assignees: University of South Florida, Tampa, FL (US); Rutgers, The State University of New Jersey, New Brunswick, NJ (US)

( * ) Notice: Subject to any disclaimer, the term of this patent is extended or adjusted under 35 U.S.C. 154(b) by 33 days.

(21) Appl. No.: 17/464,233

(22) Filed: Sep. 1, 2021

(65) Prior Publication Data
US 2022/0062274 A1 Mar. 3, 2022

Related U.S. Application Data

(60) Provisional application No. 62/706,654, filed on Sep. 1, 2020.

(51) Int. Cl.
*A61K 31/4745* (2006.01)
*A61K 31/122* (2006.01)
*A61K 31/444* (2006.01)

(52) U.S. Cl.
CPC ........ *A61K 31/4745* (2013.01); *A61K 31/122* (2013.01); *A61K 31/444* (2013.01)

(58) Field of Classification Search
CPC ................................................ A61K 31/4745
See application file for complete search history.

(56) References Cited

U.S. PATENT DOCUMENTS

| | | | |
|---|---|---|---|
| 8,703,942 B2 | 4/2014 | Chiosis et al. | |
| 9,579,315 B2 * | 2/2017 | Liggett | A61K 31/167 |
| 9,895,443 B2 | 2/2018 | Alabi et al. | |
| 10,385,072 B2 | 8/2019 | Isab et al. | |
| 2004/0152686 A1 | 8/2004 | Fenton et al. | |
| 2006/0111335 A1 | 5/2006 | Morrison et al. | |
| 2006/0111388 A1 | 5/2006 | Dibas et al. | |
| 2006/0194717 A1 | 8/2006 | Judice et al. | |
| 2011/0002877 A1 * | 1/2011 | Luo | A61K 31/4164 514/474 |
| 2015/0125550 A1 | 5/2015 | Eichler et al. | |
| 2016/0333004 A1 | 11/2016 | Ranga et al. | |

FOREIGN PATENT DOCUMENTS

| | | | | |
|---|---|---|---|---|
| CN | 104341481 A | * | 2/2015 | ............... A61K 9/08 |
| WO | WO-2008144011 A1 | * | 11/2008 | ............. A61K 31/00 |
| WO | WO-2016083490 A1 | * | 6/2016 | |

OTHER PUBLICATIONS

Machine translation of CN104341481 A (Year: 2015).*
"Treating Asthma Symptoms with Quick Relief Bronchodilators: Prescription or Over-The-Counter Inhalers", ATS Patient Education Series, Am J Respir Crit Care Med vol. 199, p. 7-p. 8, 2019 (Year: 2019).*
Grassin-Delyle et al., "Bitter Taste Receptors in Human Lung Macrophages", Front. Physiol. Oct. 2, 2019 (Year: 2019).*
Briend et al., "IL-18 associated with lung lymphoid aggregates drives IFNγ production in severe COPD", Respiratory Research, Aug. 22, 2017 (Year: 2017).*
Ozkaya et al., "The Objective Evaluation of obstructive pulmonary diseases with spirometry", Int J Chron Obstruct Pulmon Dis, Aug. 25, 2016, pp. 2009-2015 (Year: 2016).*
Kim et al., "Identification and Characterization of Novel Bronchodilator Agonists Acting at Human Airway Smooth Muscle Cell TAS2R5", ACE Pharmacology and Translational Science, Nov. 5, 2020 (Year: 2020).*
"Obstructive lung disease", Wikipedia, Aug. 31, 2021 (Year: 2021).*
Tracy et al., "Allergic Bronchopulmonary Aspergillosis", Journal of Fungi, Mar. 31, 2016 (Year: 2016).*
An, S. S., and Liggett, S. B. (2018) Taste and smell GPCRs in the lung: Evidence for a previously unrecognized widespread chemosensory system, Cell Signal 41, 82-88.
An, S. S., Fabry, B., Trepat, X., Wang, N., and Fredberg, J. J. (2006) Do biophysical properties of the airway smooth muscle in culture predict airway hyperresponsiveness?, Am J Respir Cell Mol Biol. 35, 55-64.
An, S. S., Wang, W. C., Koziol-White, C. J., Ahn, K., Lee, D. Y., Kurten, R. C., Panettieri, R. A., Jr., and Liggett, S. B. (2012) TAS2R activation promotes airway smooth muscle relaxation despite beta(2)-adrenergic receptor tachyphylaxis, Am J Physiol Lung Cell Mol Physiol 303, L304-311.
Bhagat, R., Kalra, S., Swystun, V. A., and Cockcroft, D. W. (1995) Rapid onset of tolerance to the bronchoprotective effect of salmeterol, Chest 108, 1235-1239.
Booth, H., Bish, R., Walters, J., Whitehead, F., and Walters, E. H. (1996) Salmeterol tachyphylaxis in steroid treated asthmatic subjects, Thorax 51, 1100-1104.
Borghardt, J. M., Kloft, C., and Sharma, A. (2018) Inhaled Therapy in Respiratory Disease: The Complex Interplay of Pulmonary Kinetic Processes, Can Respir J 2018, 1-64.
Brittain, R. T., Farmer, J. B., and Marshall, R. J. (1973) Some observations on the—adrenoceptor agonist properties of the isomers of salbutamol, Br J Pharmacol 48, 144-147.
Chandrashekar, J., Mueller, K. L., Hoon, M. A., Adler, E., Feng, L., Guo, W., Zuker, C. S., and Ryba, N. J. (2000) T2Rs function as bitter taste receptors, Cell 100, 703-711.

(Continued)

*Primary Examiner* — Jeffrey T. Palenik
*Assistant Examiner* — Gillian A Hutter
(74) *Attorney, Agent, or Firm* — Meunier Carlin & Curfman LLC

(57) ABSTRACT

Disclosed herein are compounds useful for treating obstructive lung diseases. The compounds are TAS2Rs agonists and may further be used to treat disorders and conditions implicated by TAS2R. In some instances the disclosed compounds can be used to treat asthma.

16 Claims, 13 Drawing Sheets

(56) References Cited

OTHER PUBLICATIONS

Cheung, D., Timmers, M. C., Zwinderman, A. H., Bel, E. H., Dijkman, J. H., and Sterk, P. J. (1992) Long-term effects of a long acting b2-adrenoceptor agonist, salmeterol, on airway hyperresponsiveness in patients with mild asthma, N Engl J Med 327, 1198-1203.

Clark, A. A., Liggett, S. B., and Munger, S. D. (2012) Extraoral bitter taste receptors as mediators of off-target drug effects, FASEB J 26, 4827-4831.

Cox, P. B., Gregg, R. J., and Vasudevan, A. (2012) Abbott Physicochemical Tiering (APT)—a unified approach to HTS triage, Bioorg Med Chem 20, 4564-4573.

Deb, J., Lakshman, T. R., Ghosh, I., Jana, S. S., and Paine, T. K. (2020) Mechanistic studies of in vitro anti-proliferative and anti-inflammatory activities of the Zn(ii)-NSAID complexes of 1,10-phenanthroline-5,6-dione in MDA-MB-231 cells, Dalton Trans 49, 11375-11384.

Deshpande, D. A., Robinett, K. S., Wang, W. C., Sham, J. S., An, S. S., and Liggett, S. B. (2011) Bronchodilator activity of bitter tastants in human tissue, Nature Medicine 17, 776-778.

Deshpande, D. A., Wang, W. C., McIlmoyle, E. L., Robinett, K. S., Schillinger, R. M., An, S. S., Sham, J. S., and Liggett, S. B. (2010) Bitter taste receptors on airway smooth muscle bronchodilate by localized calcium signaling and reverse obstruction, Nature Medicine 16, 1299-1304.

Goldie, R. G., Spina, D., Henry, P. J., Lulich, K. M., and Paterson, J. W. (1986) In vitro responsiveness of human asthmatic bronchus to carbachol, histamine, b-adrenoreceptor agonists and theophylline, Br J Clin Pharmacol 22, 669-676.

Grainger, J., Woodman, K., Peace, N., Crane, J., Burgess, C., Keane, A., and Beasley, R. (1991) Prescribed fenoterol and death from asthma in New Zealand, 1981-7: a further case-control study, Thorax 46, 105-111.

Grove, A., and Lipworth, B. J. (1995) Bronchodilator subsensitivity to salbutamol after twice daily salmeterol in asthmatic patients, Lancet 346, 201-206.

Gupta, M. K., Asosingh, K., Aronica, M., Comhair, S., Cao, G., Erzurum, S., Panettieri, R. A., Jr., and Naga Prasad, S. V. (2015) Defective Resensitization in Human Airway Smooth Muscle Cells Evokes beta-Adrenergic Receptor Dysfunction in Severe Asthma, PLoS One 10, e0125803.

Hawkins, G. A., Tantisira, K., Meyers, D. A., Ampleford, E. J., Klanderman, B., Liggett, S. B., Peters, S. P., Weiss, S. T., and Bleecker, E. R. (2006) Sequence, haplotype and association analysis of ADRbeta2 in a multiethnic asthma case-control study, Am J Respir Crit Care Med 174, 1101-1109.

Holst, B., Elling, C. E., & Schwartz, T. W. (2002). Metal ion-mediated agonism and agonist enhancement in melanocortin MC1 and MC4 receptors. Journal of Biological Chemistry, 277(49), 47662-47670.

Israel, E., Chinchilli, V. M., Ford, J. G., Boushey, H. A., Cherniack, R., Craig, T. J., Deykin, A., Fagan, J. K., Fahy, J. V., Fish, J., Kraft, M., Kunselman, S. J., Lazarus, S. C., Lemanske, R. F., Jr., Liggett, S. B., Martin, R. J., Mitra, N., Peters, S. P., Silverman, E., Sorkness, C. A., Szefler, S. J., Wechsler, M. E., Weiss, S. T., and Drazen, J. M. (2004) Use of regularly scheduled albuterol treatment in asthma: genotype-stratified, randomised, placebo-controlled cross-over trial, Lancet 364, 1505-1512.

Kim, D., Woo, J. A., Geffken, E., An, S. S., and Liggett, S. B. (2017) Coupling of airway smooth muscle bitter taste receptors to intracellular signaling and relaxation is via Galphai1,2,3, Am J Respir Cell Mol Biol 56, 762-771.

Kim, U., Wooding, S., Ricci, D., Jorde, L. B., and Drayna, D. (2005) Worldwide haplotype diversity and coding sequence variation at human bitter taste receptor loci, Hum Mutat 26, 199-204.

Kraan, J., Koeter, G. H., van der Mark, T. W., Sluiter, H. J., and De Vries, K. (1985) Changes in bronchial hyperreactivity induced by 4 weeks of treatment with antiasthmatic drugs in patients with allergic asthma: a comparison between budesonide and terbutaline, J Allergy Clin Immunol 76, 636-636.

Linden, A., Bergendal, A., Ullman, A., Skoogh, B. E., and Lofdahl, C. G. (1993) Salmeterol, formoterol, and salbutamol in the isolated guinea pig trachea: differences in maximum relaxant effect and potency but not in functional antagonism, Thorax 48, 547-553.

Lotvall, J. (2001) Pharmacological similarities and differences between beta2-agonists, Respir Med 95 Suppl B, S7-11.

Malmstrom, K., Rodriguez-Gomez, G., Guerra, J., Villaran, C., Pineiro, A., Wei, L. X., Seidenberg, B. C., and Reiss, T. F. (1999) Oral montelukast, inhaled beclomethasone, and placebo for chronic asthma. A randomized, controlled trial. Montelukast/Beclomethasone Study Group, Ann Intern Med 130, 487-495.

Matera, M. G., Page, C. P., and Cazzola, M. (2011) Novel bronchodilators for the treatment of chronic obstructive pulmonary disease, Trends Pharmacol Sci 32, 495-506.

Matera, M. G., Page, C. P., Calzetta, L., Rogliani, P., and Cazzola, M. (2020) Pharmacology and Therapeutics of Bronchodilators Revisited, Pharmacol Rev 72, 218-252.

Meyerhof, W., Batram, C., Kuhn, C., Brockhoff, A., Chudoba, E., Bufe, B., Appendino, G., and Behrens, M. (2010) The molecular receptive ranges of human TAS2R bitter taste receptors, Chem Senses 35, 157-170.

Motulsky, H., and Christopoulos, A. (2004) Fitting Models to Biological Data Using Linear and Nonlinear Regression a Practical Guide to Curve Fitting, pp. 13-46, Oxford University Press, USA, Oxford.

Motulsky, H., and Neubig, R. (2002) Analyzing radioligand binding data, Curr Protoc Neurosci Chapter 7, Unit 7 5.

Nelson, H. S., Weiss, S. T., Bleecker, E. R., Yancey, S. W., and Dorinsky, P. M. (2006) The Salmeterol Multicenter Asthma Research Trial: a comparison of usual pharmacotherapy for asthma or usual pharmacotherapy plus salmeterol, Chest 129, 15-26.

Newnham, D. M., Grove, A., McDevitt, D. G., and Lipworth, B. J. (1995) Subsensitivity of bronchodilator and systemic b2 adrenoceptor responses after regular twice daily treatment with eformoterol dry power in asthmatic patients, Thorax 50, 497-504.

Nowak, S., Di Pizio, A., Levit, A., Niv, M. Y., Meyerhof, W., and Behrens, M. (2018) Reengineering the ligand sensitivity of the broadly tuned human bitter taste receptor TAS2R14, Biochimica et biophysica acta. General subjects 1862, 2162-2173.

Robinett, K. S., Deshpande, D. A., Malone, M. M., and Liggett, S. B. (2011) Agonist-promoted homologous desensitization of human airway smooth muscle bitter taste receptors, Am J Respir Cell Mol Biol 45, 1069-1074.

Robinett, K. S., Koziol-White, C. J., Akoluk, A., An, S. S., Panettieri, R. A., Jr., and Liggett, S. B. (2014) Bitter taste receptor function in asthmatic and nonasthmatic human airway smooth muscle cells, Am J Respir Cell Mol Biol 50, 678-683.

Roux, F. J., Grandordy, B., and Douglas, J. S. (1996) Functional and binding characteristics of long-acting beta 2-agonists in lung and heart, Am J Respir Crit Care Med 153, 1489-1495.

Salpeter, S. R., Buckley, N. S., Ormiston, T. M., and Salpeter, E. E. (2006) Meta-Analysis: effect of long-acting b-agonists on severe asthma exacerbations and asthma-related deaths, Ann Intern Med 144, 904-912.

Salpeter, S. R., Wall, A. J., and Buckley, N. S. (2010) Long-acting beta-agonists with and without inhaled corticosteroids and catastrophic asthma events, Am J Med 123, 322-328.

Scott, M. G., Swan, C., Jobson, T. M., Rees, S., and Hall, I. P. (1999) Effects of a range of beta2 adrenoceptor agonists on changes in intracellular cyclic AMP and on cyclic AMP driven gene expression in cultured human airway smooth muscle cells, Br J Pharmacol 128, 721-729.

Sears, M. R. (1998) Role of b-agonists in asthma fatalities, In Fatal Asthma (Sheffer, A. L., Ed.), pp. 457-481, Marcel Dekker, Inc., New York.

Sears, M. R., and Taylor, D. R. (1994) The b2-agonist controversy: Observations, explanations and relationship to asthma epidemiology, Drug Safety 11, 259-283.

(56) References Cited

OTHER PUBLICATIONS

Sears, M. R., Taylor, D. R., Print, C. G., Lake, D. C., Qingoing, L., Flannery, E. M., Yates, D., Lucas, M. K., and Herbison, G. P. (1990) Regular inhaled beta-agonist treatment in bronchial asthma, Lancet 336, 1391-1396.

Silverman, E. K., Kwiatkowski, D. J., Sylvia, J. S., Lazarus, R., Drazen, J. M., Lange, C., Laird, N. M., and Weiss, S. T. (2003) Family-based association analysis of beta2-adrenergic receptor polymorphisms in the childhood asthma management program, J Allergy Clin Immunol 112, 870-876.

Soares, S., Kohl, S., Thalmann, S., Mateus, N., Meyerhof, W., and De Freitas, V. (2013) Different phenolic compounds activate distinct human bitter taste receptors, J Agric Food Chem 61, 1525-1533.

Tay, C. X., Quah, S. Y., Lui, J. N., Yu, V. S., and Tan, K. S. (2015) Matrix Metalloproteinase Inhibitor as an Antimicrobial Agent to Eradicate Enterococcus faecalis Biofilm, J Endod 41, 858-863.

Woo, J. A., Castano, M., Goss, A., Kim, D., Lewandowski, E. M., Chen, Y., and Liggett, S. B. (2019) Differential long-term regulation of TAS2R14 by structurally distinct agonists, FASEB J 33, 12213-12225.

Yang, X., Chen, L., Liu, Y., Yang, Y., Chen, T., Zheng, W., . . . & He, Q. Y. (2012). Ruthenium methylimidazole complexes induced apoptosis in lung cancer A549 cells through intrinsic mitochondrial pathway. Biochimie, 94(2), 345-353.

\* cited by examiner

BRONCHODILATORS FOR TREATING OBSTRUCTIVE LUNG DISEASE

CROSS-REFERENCE TO RELATED APPLICATION

This application claims the benefit of U.S. Provisional Application 62/706,654, filed Sep. 1, 2020, the contents of which are hereby incorporated in its entirety.

ACKNOWLEDGEMENT OF GOVERNMENT SUPPORT

This invention was made with government support under grant/contract HL114471 awarded by the National Institutes of Health. The government has certain rights in the invention.

FIELD OF THE INVENTION

The invention is directed to compounds, compositions, and methods for treating obstructive lung diseases, including asthma.

BACKGROUND

Bitter taste receptors (TAS2Rs) are members of the G protein coupled receptor (GPCR) superfamily of receptors, and traditionally were thought to have expression confined to taste cells where they detect bitter substances. The human genome encodes 25 TAS2R subtypes, with varying degrees of specificities to bitter tastants. Some subtypes are described as being "broadly tuned" while others appear to have highly restrictive requirements for agonist binding and activation. Recent studies have shown that TAS2Rs are expressed on multiple cell types and tissues throughout the body, representing a previously unrecognized chemosensory system responding to endogenous and exogenous substances, including potential novel therapeutic targets.

Of particular interest has been the delineation of six TAS2R subtypes (TAS2Rs 4, 5, 10, 14, 19, 31) that are ex-pressed on human airway smooth muscle (HASM) cells. TAS2R activation in these cells results in coupling of the receptor to the Gαi family of G proteins with a subsequent increase in intracellular $Ca^{2+}$ ($[Ca^{2+}]_i$) in microdomains that leads to marked HASM relaxation. This has prompted investigations into the use of TAS2R agonists as a potential treatment for obstructive lung diseases such as asthma, where HASM contraction is a main mechanism of airflow restriction. Five of the aforementioned six TAS2R subtypes appear to be broadly tuned, being activated by compounds with a wide-ranging structural properties, albeit with typically low apparent affinities. These properties may be due to the evolution of TAS2Rs on taste cells in order to detect the large number bitter tasting toxic substances found in plants. This diversity is illustrated by studies with TAS2R14, which show that it is activated by quinine, aristolochic acid, chlorhexidine, and flufenamic acid, as well as >29 other known compounds. Furthermore, many of these agonists also activate other TAS2R sub-types not expressed on HASM, but found in other organs such as heart, thyroid, pancreas, and uterus. For drug development, this lack of more specific high-affinity binding requirements of TAS2R binding pockets for activation represents a challenge for identifying receptor ligands for therapeutic purposes.

Currently, the only available direct bronchodilators are $β_2$-adrenergic receptor ($β_2AR$) agonists, also called "β-agonists". These agents activate the cell surface $β_2AR$ on HASM and activate Gαs, stimulating adenylyl cyclase and increasing cellular cAMP and activation of protein kinase A, which leads to relaxation. β-agonists are associated with a number of adverse effects, and about one-half of asthmatics fail to reach optimal control. Thus, efforts to find new classes of direct bronchodilators targeting a number of HASM proteins are underway. These include not only TAS2Rs, but Rho kinase inhibitors, prostanoid receptor agonists, peroxisome proliferator-activated receptor γ agonists and pepducins that modify GPCR signaling. Our studies of HASM TAS2Rs for potential new bronchodilator targets are based on experiments where we find a high level of efficacy for relaxation of human bronchi, no effect of the asthma cellular phenotype on TAS2R function, additive effects with β-agonists without cross-desensitization, and their distinct mechanism of action.

The remains a need for improved bronchodilating agents. There remains a need for improved TAS2R5 agonists. There remains a need for improved methods of treating obstructive lung disease, including asthma.

SUMMARY

In accordance with the purposes of the disclosed materials and methods, as embodied and broadly described herein, the disclosed subject matter, in one aspect, relates to compounds, compositions and methods of making and using compounds and compositions. In specific examples, the compounds have the formula:

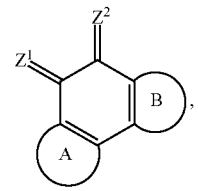

or a pharmaceutically acceptable salt thereof, wherein
ring A represents a carbocyclic or heterocyclic ring system;
ring b represents a carbocyclic or heterocyclic ring system;
$Z^1$ is O, S, or $NR^a$; wherein $R^a$ is H, $C_{1-8}$alkyl, or $C_{1-8}$alkoxy; and
$Z^2$ is O, S, or $NR^b$; wherein $R^b$ is H, $C_{1-8}$alkyl, or $C_{1-8}$alkoxy.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments are set forth in the descriptions below. Other features, objects, and advantages will be apparent from the description and from the claims.

DETAILED DESCRIPTION

Figure 1:
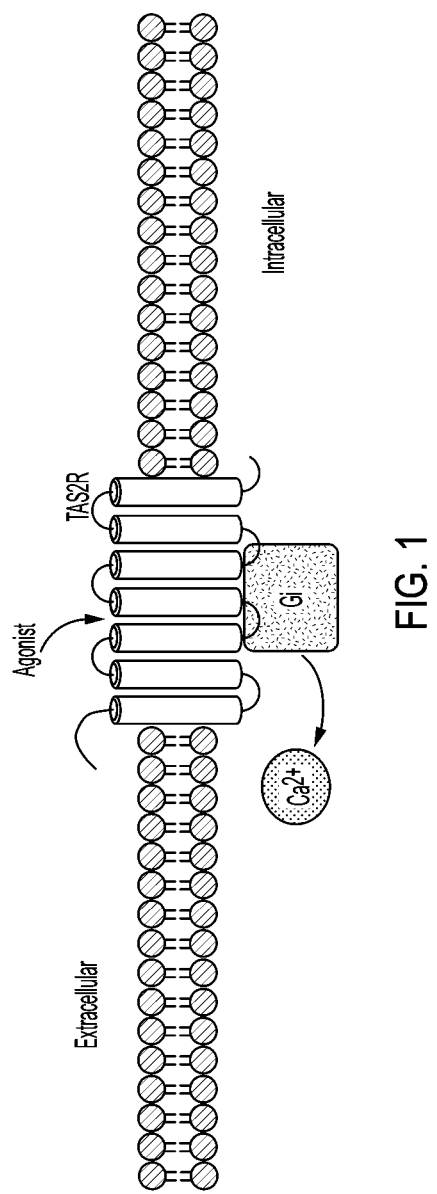
FIG. 1 depicts the general signaling paradigm of TAS2Rs in airway smooth muscle cells. Agonist binds to residues in a pocket formed by the hydrophobic transmembrane domains of the receptor, resulting in a conformation that binds and activates the heterotrimeric G protein Gi, ultimately causing an increase in $[Ca^{2+}]_i$.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein "aromatic" refers to an unsaturated cyclic molecule having $4n+2\pi$ electrons, wherein n is any integer. The term "non-aromatic" refers to any saturated system or unsaturated cyclic molecule which does not fall within the definition of aromatic.

The term "acyl" refers to groups —C(O)R, where R is hydrogen, alkyl, alkenyl, alkynyl, carbocyclyl, or heterocyclyl, as defined herein. Unless stated otherwise specifically in the specification, acyl can be optionally substituted.

"Alkyl" or "alkyl group" refers to a fully saturated, straight or branched hydrocarbon chain radical having from one to forty carbon atoms, and which is attached to the rest of the molecule by a single bond. Alkyls comprising any number of carbon atoms from 1 to 20 are included. An alkyl comprising up to 40 carbon atoms is a $C_1$-$C_{10}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_8$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted.

"Alkenyl" or "alkenyl group" refers to a straight or branched hydrocarbon chain radical having from two to forty carbon atoms, and having one or more carbon-carbon double bonds. Each alkenyl group is attached to the rest of the molecule by a single bond. Alkenyl group comprising any number of carbon atoms from 2 to 40 are included. An alkenyl group comprising up to 40 carbon atoms is a $C_2$-$C_{10}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally.

"Alkoxy" refers to the group —OR, where R is alkyl, alkenyl, alkynyl, cycloalkyl, or heterocyclyl as defined herein. Unless stated otherwise specifically in the specification, alkoxy can be optionally substituted.

"Alkylcarbamoyl" refers to the group —O—C(O)—NR$_a$R$_b$, where R$_a$ and R$_b$ are the same or different and independently an alkyl, alkenyl, alkynyl, aryl, heteroaryl, cycloalkyl, or heterocyclyl group, as defined herein, or R$_a$R$_b$ can be taken together to form a heterocyclyl group, as defined herein. Unless stated otherwise specifically in the specification, alkylcarbamoyl can be optionally substituted.

"Alkylcarboxamidyl" refers to the group —C(O)—NR$_a$R$_b$, where R$_a$ and R$_b$ are the same or different and independently an alkyl, alkenyl, alkynyl, aryl, heteroaryl, cycloalkyl, cycloalkenyl, cycloalkynyl, or heterocyclyl group, as defined herein, or R$_a$R$_b$ can be taken together to form a cycloalkyl group, as defined herein. Unless stated otherwise specifically in the specification, alkylcarboxamidyl can be optionally substituted.

"Alkoxycarbonyl" refers to the group —C(O)OR, where R is alkyl, alkenyl, alkynyl, aryl, heteroaryl, cycloalkyl, cycloalkenyl, cycloalkynyl, or heterocyclyl group, as defined herein. Unless stated otherwise specifically in the specification, alkoxycarbonyl can be optionally substituted.

"Alkylthio" refers to the —SR or —S(O)$_{n=1\text{-}2}$—R, where R is alkyl, alkenyl, alkynyl, cycloalkyl, cycloalkenyl, cycloalkynyl, or hetereocyclyl, as defined herein. Unless stated otherwise specifically in the specification, alkylthio can be optionally substituted.

"Arylthio" refers to the —SR or —S(O)$_{n=1\text{-}2}$—R, where R is aryl or hetereoaryl, as defined herein. Unless stated otherwise specifically in the specification, arylthio can be optionally substituted.

"Alkynyl" or "alkynyl group" refers to a straight or branched hydrocarbon chain radical having from two to forty carbon atoms, and having one or more carbon-carbon triple bonds. Each alkynyl group is attached to the rest of the molecule by a single bond. Alkynyl group comprising any number of carbon atoms from 2 to 40 are included. An alkynyl group comprising up to 40 carbon atoms is a $C_2$-$C_{10}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Unless stated otherwise specifically in the specification, the carbocyclyl can be a monocyclic, bicyclic, tricyclic or tetracyclic ring system, which can include fused or bridged ring systems Carbocyclic rings include cycloalkyl, cycloalkenyl, and cycloalkynyl as defined herein. In some embodiments, the carbocyclyl is monovalent and is attached to the rest of molecule through a single bond. In some embodiments, the carbocyclyl is divalent and is independently attached to two moieties through single bonds. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo [2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered ring radical, which consists of two to fourteen carbon atoms and from one to eight heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be aromatic, partially saturated, or fully saturated. Examples of heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. In some embodiments, the heterocyclyl is monovalent and is attached to the rest of molecule through a single bond. In some embodiments, the heterocyclyl is divalent and is independently attached to two moieties through single bonds. Unless stated otherwise specifically in the specification, a heterocyclyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aryloxy" refers to groups —OAr, where Ar is an aryl or heteroaryl group as defined herein. Unless otherwise stated specifically in the specification, the aryloxy group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Aralkyl" refers to a radical of the formula —$R_b$—$R_c$ where $R_b$ is an alkylene, alkenylene or alkynylene group as defined above and $R^c$ is one or more aryl radicals as defined above, for example, benzyl, diphenylmethyl and the like. Unless stated otherwise specifically in the specification, an aralkyl group can be optionally substituted.

The term "substituted" used herein means any of the above groups (i.e., alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio) wherein at least one atom is replaced by a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —SO$_2$NR$_g$R$_h$. "Substituted also means any of the above groups in which one or more hydrogen atoms are replaced with —C(=O) R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more atoms are replaced by an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. "Substituted" can also mean an amino acid in which one or more atoms on the side chain are replaced by alkyl, alkenyl, alkynyl, acyl, alkylcarboxamidyl, alkoxycarbonyl, carbocyclyl, heterocyclyl, aryl, or heteroaryl. In addition, each of the foregoing substituents can also be optionally substituted with one or more of the above substituents.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture. Unless stated to the contrary, a formula depicting one or more stereochemical features does not exclude the presence of other isomers.

Unless stated to the contrary, a substituent drawn without explicitly specifying the point of attachment indicates that the substituent may be attached at any possible atom. For example, in a benzofuran depicted as:

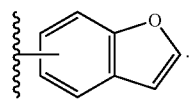

the substituent may be present at any one of the six possible carbon atoms.

As used herein, the term "null," when referring to a possible identity of a chemical moiety, indicates that the group is absent, and the two adjacent groups are directly bonded to one another. By way of example, for a genus of compounds having the formula CH$_3$—X—CH$_3$, if X is null, then the resulting compound has the formula CH$_3$—CH$_3$.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

As used herein, the term "about" or "approximately" refers to a quantity, level, value, number, frequency, percentage, dimension, size, amount, weight or length that varies by acceptable levels in the art. In some embodiments, the amount of variation may be as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or +1% about a reference quantity, level, value, number, frequency, percentage, dimension, size, amount, weight or length.

A numerical range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Disclosed herein are bronchodilating compounds and methods of using the disclosed bronchodilating compounds in the treatment of obstructive lung diseases. In some embodiments, the compounds have the formula:

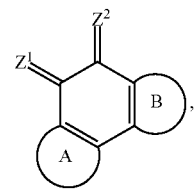

or a pharmaceutically acceptable salt thereof, wherein
ring A represents a carbocyclic or heterocyclic ring system;
ring b represents a carbocyclic or heterocyclic ring system;

$Z^1$ is O, S, or $NR^a$; wherein $R^a$ is H, OH, $C_{1-8}$alkyl, or $C_{1-8}$alkoxy; and $Z^2$ is O, S, or $NR^b$; wherein $R^b$ is H, OH, $C_{1-8}$alkyl, or $C_{1-8}$alkoxy.

In some embodiments, $Z^1$ and $Z^2$ are each O. In other embodiments, $Z^1$ is $NR^a$ and $Z^2$ is O. In other embodiments, $Z^2$ is $NR^a$ and $Z^1$ is O. In further embodiments $Z^1$ and $Z^2$ are each $NR^a$. Exemplary $R^a$ groups include H, OH, $C_{1-2}$alkyl, and $C_{1-2}$alkoxy.

In some embodiments, ring A can include an $sp^2$ hybridized nitrogen atom bonded to the central ring para to the $Z^2$ bearing carbon atom. Such compounds may be depicted by the formula:

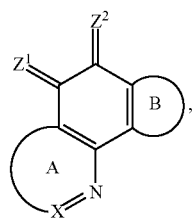

wherein

X is N or $CR^1$, wherein $R^1$ is selected from $R^a$, $OR^a$, $N(R^a)_2$, F, Cl, Br, I, $NO_2$, CN, wherein $R^a$ is in each case selected from H, $C_{1-8}$alkyl, $C_{2-8}$alkenyl; $C_{2-8}$alkynyl. Suitable ring A systems include:

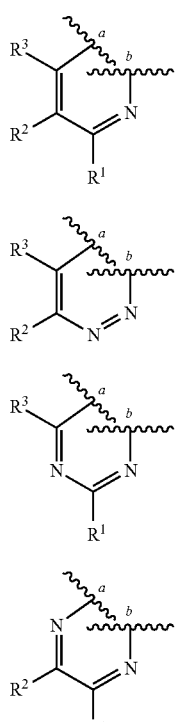

Ring A-1

Ring A-2

Ring A-3

Ring A-4

Ring A-5

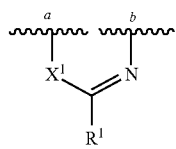

Ring A-6 wherein wavy line "a" represent the point of attachment to the carbon ortho to the $Z^1$ bearing carbon, and wavy line "b" represents the point of attachment to the carbon para to the $Z^2$ bearing carbon;

$X^1$ is O, S, or $NR^4$ $R^2$ is selected from $R^b$, $OR^b$, $N(R^b)_2$, F, Cl, Br, I, $NO_2$, CN, wherein $R^b$ is in each case selected from H, $C_{1-8}$alkyl, $C_{2-8}$alkenyl; $C_{2-8}$alkynyl;

$R^3$ is selected from $R^c$, $OR^c$, $N(R^c)_2$, F, Cl, Br, I, $NO_2$, CN, wherein $R^c$ is in each case selected from H, $C_{1-8}$alkyl, $C_{2-8}$alkenyl; $C_{2-8}$alkynyl;

$R^4$ is H or $C_{1-8}$alkyl, $C_{2-8}$alkenyl; $C_{2-8}$alkynyl;

wherein any two or more of $R^1$, $R^2$, $R^3$, and $R^4$ may together form a ring; and wherein either $R^3$ or $R^4$ may form a ring with $R^a$.

In some embodiments ring B can be an aromatic or heteroaromatic system having the formula:

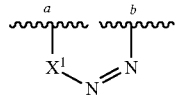

Ring B-1

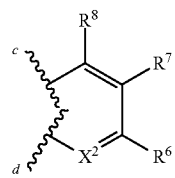

Ring B-2

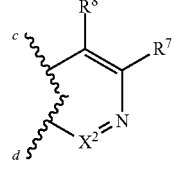

Ring B-3

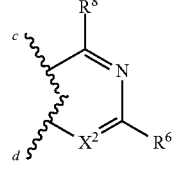

Ring B-4

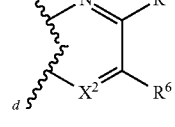

Ring B-5

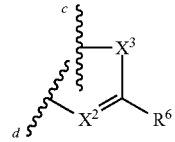

-continued

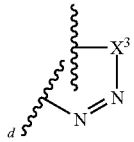
Ring B-6 wherein wavy line "c" represent the point of attachment to the carbon ortho to the $Z^2$ bearing carbon, and wavy line "d" represents the point of attachment to the carbon para to the $Z^1$ bearing carbon;

$X^2$ is N or $CR^5$;

$X^3$ is N or $CR^9$;

$R^5$ is H or $C_{1-8}$alkyl, $C_{2-8}$alkenyl; $C_{2-8}$alkynyl;

$R^9$ is H or $C_{1-8}$alkyl, $C_{2-8}$alkenyl; $C_{2-8}$alkynyl;

$R^6$ is selected from $R^d$, $OR^d$, $N(R^d)_2$, F, Cl, Br, I, $NO_2$, CN, wherein $R^d$ is in each case selected from H, $C_{1-8}$alkyl, $C_{2-8}$alkenyl; $C_{2-8}$alkynyl;

$R^7$ is selected from $R^e$, $OR^e$, $N(R^e)_2$, F, Cl, Br, I, $NO_2$, CN, wherein $R^e$ is in each case selected from H, $C_{1-8}$alkyl, $C_{2-8}$alkenyl; $C_{2-8}$alkynyl;

$R^8$ is selected from $R^f$, $OR^f$, $N(R^f)_2$, F, Cl, Br, I, $NO_2$, CN, wherein $R^f$ is in each case selected from H, $C_{1-8}$alkyl, $C_{2-8}$alkenyl; $C_{2-8}$alkynyl;

wherein any two or more of $R^5$, $R^6$, $R^7$, and $R^8$ may together form a ring; and wherein either $R^8$ or $R^9$ may form a ring with $R^b$.

Exemplary compounds include those in which $Z^1$ and $Z^2$ are each O, ring A is Ring A-1, and ring B is Ring B-1, wherein $X^2$ is N or CH. In other embodiments, ring A is Ring A-1, and ring B is Ring B-2, wherein $X^2$ is N or CH. In other embodiments, ring A is Ring A-1, and ring B is Ring B-3, wherein $X^2$ is N or CH. In other embodiments, ring A is Ring A-1, and ring B is Ring B-4, wherein $X^2$ is N or CH.

In some embodiments, the compound has the formula:

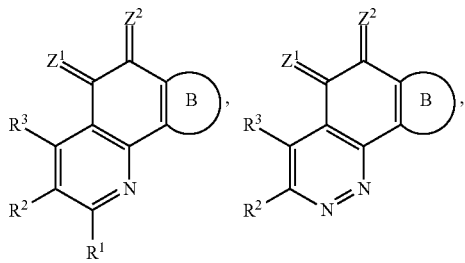

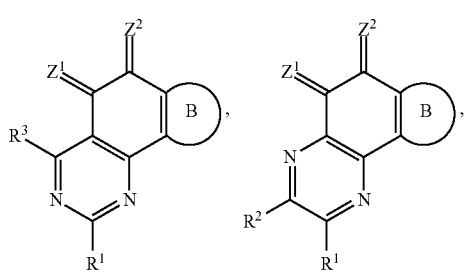

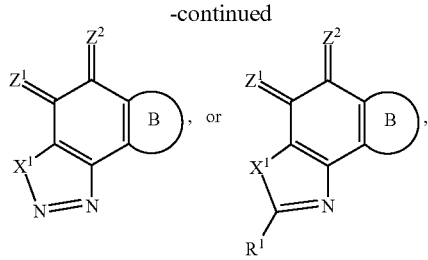

wherein $Z^1$, $Z^2$, ring B, $R^1$, $R^2$, $R^3$, and $X^1$ are as defined above. Preferably, $Z^1$ and $Z^2$ are each O In some embodiments, the compound has the formula:

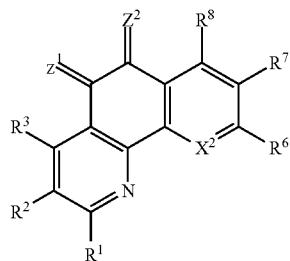

wherein $Z^1$, $Z^2$, $R^1$, $R^2$, $R^3$, $R^6$, $R^7$, $R^8$, and $X^2$ are as defined above In certain embodiments, ring B is Ring B-1, B-2, or B-3, and $Z^2$ is $NR^a$. In further embodiments, $R^a$ can together form a ring with $R^8$. Exemplary systems include:

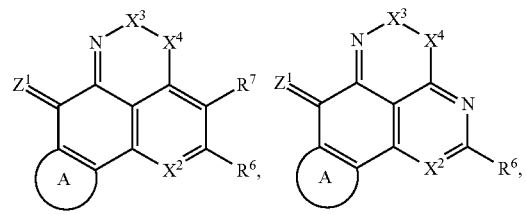

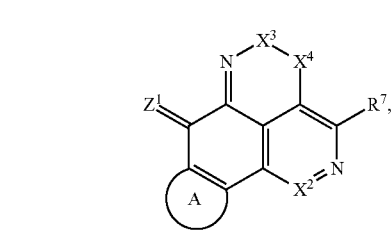

wherein ring A, $Z^1$, $X^2$, $R^6$, and $R^7$ are as defined above, and $X^3$ is selected from null, O, $C_{1-3}$alkylene, and $X^4$ is selected from null, O, $C_{1-3}$alkylene, provided that $X^3$ and $X^4$ are not both null, and also provided that $X^3$ and $X^4$ are not both O.

In certain embodiments, ring A is Ring A-1, A-2, or A-3, and $Z^1$ is $NR^a$. In further embodiments, $R^a$ can together form a ring with $R^3$. Exemplary systems include:

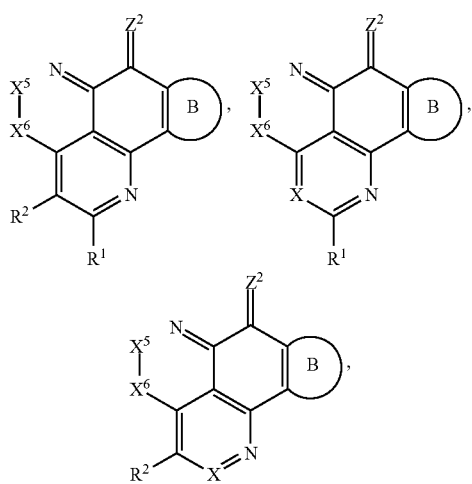

wherein ring B, $Z^2$, X, $R^1$, and $R^2$ are as defined above, and $X^5$ is selected from null, O, $C_{1\text{-}3}$alkylene, and $X^6$ is selected from null, O, $C_{1\text{-}3}$alkylene, provided that $X^3$ and $X^4$ are not both null, and that $X^3$ and $X^4$ are not both O.

It is further contemplated that in some embodiments, both $Z^1$ and $Z^2$ are $NR^a$, and each $R^a$ forms a ring with $R^3$ and $R^8$, e.g.,

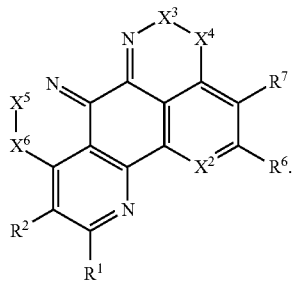

Also provided herein are methods of use of the compounds or compositions described herein. Also provided herein are methods for treating a disease or pathology in a subject in need thereof comprising administering to the subject an effective amount of any of the compounds or compositions described herein.

Disclosed are methods of treating an obstructive lung disease or condition in a subject, comprising administering a therapeutically effective amount of a pharmaceutical composition comprising one or more compounds disclosed herein to a subject in need of treatment. In particular aspects, the obstructive lung disease or condition can be, e.g., asthma, chronic obstructive pulmonary disease (COPD), emphysema or bronchitis.

In a second aspect, provided herein are methods of inducing bronchodilation in a subject, comprising administering a therapeutically effective amount of a pharmaceutical composition comprising one or more compounds disclosed herein to a subject in need of bronchodilation.

In a third aspect, provided herein are methods of relaxing airway smooth muscle (ASM) in a subject, comprising administering a therapeutically effective amount of a pharmaceutical composition comprising one or more compounds disclosed herein to a subject in need of ASM relaxation.

In a fourth aspect, provided herein are methods of treating or preventing bronchoconstriction or bronchospasm in a subject, comprising administering a therapeutically effective amount of a pharmaceutical composition comprising one or more compounds disclosed herein to a subject in need of treatment or prevention of bronchoconstriction or bronchospasm.

The obstructive lung diseases and conditions encompassed by the present invention include any respiratory condition or disease, whether acute or chronic, characterized by impairment of airflow into and/or out of the lungs of a subject. Obstructive lung diseases and conditions include, e.g., asthma, chronic obstructive pulmonary disease (COPD), emphysema and bronchitis, as well as cystic fibrosis, bronchiectasis, bronchiolitis, and allergic bronchopulmonary aspergillosis. Another such obstructive lung disease or condition that can be treated or prevented by administering compounds as described herein includes bronchoconstriction or bronchospasm that can be caused, e.g., by inhalation of a noxious compound such as smoke or a corrosive chemical; by a respiratory infection; or by anaphylaxis such as that caused by sepsis or an allergic reaction to a food (e.g., peanuts), a drug (e.g., penicillin), an insect sting or bite, pollen, mold, dust mites, latex, or other substances; or by other triggers of bronchoconstriction or bronchospasm. For example, the compounds can be administered to prevent (or treat) bronchospasm induced by exercise or air pollution. In another example, the compounds can be administered before or during placement of a breathing tube to prevent (or treat) bronchospasm induced by placement of the tube. The compounds of the invention can be administered to healthy individuals in situations in which it might be desirable to increase bronchodilation to improve oxygen uptake, e.g., in lower oxygen environments (such as several thousand feet above sea level) or to improve athletic performance.

The pharmaceutical compositions of the present invention comprising one or more compounds disclosed herein may also comprise one or more of a carrier, diluent and excipient (e.g., a pharmaceutically acceptable carrier, diluent, or excipient), depending on the identity of the compound. By "pharmaceutically acceptable" is meant a material that is not biologically or otherwise undesirable, i.e., the material may be administered to an individual along with the compound without causing any undesirable biological effects or interacting in a deleterious manner with any of the components of the pharmaceutical composition in which it is contained. Conventional pharmaceutical practice may be employed to provide suitable formulations or compositions to administer such compositions to subjects. The terms specifically exclude cell culture medium. Suitable diluents (for both dry and liquid pharmaceutical formulations) are well known to those skilled in the art and include saline, buffered saline, dextrose (e.g., 5% dextrose in water), water, glycerol, ethanol, propylene glycol, polysorbate 80 (Tween-80™), poly (ethylene) glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717).

Carriers are compounds and substances that improve and/or prolong the delivery of an active ingredient to a subject in the context of a pharmaceutical formulation. Carriers may serve to prolong the in vivo activity of a drug or slow the release of the drug in a subject, using controlled-release technologies. Carriers may also decrease drug metabolism in a subject and/or reduce the toxicity of the drug. Carriers can also be used to target the delivery of the drug to particular cells or tissues in a subject. Common carriers (both hydrophilic and hydrophobic carriers) include fat emulsions, lipids, PEGylated phospholids, liposomes and lipospheres, microspheres (including those made of biodegradable polymers or albumin), polymer matrices, biocompatible polymers, protein-DNA complexes, protein conjugates, erythrocytes, vesicles and particles.

Excipients included in a pharmaceutical composition have different purposes depending, for example on the nature of the drug, and the mode of administration. Examples of generally used excipients include, without limitation: stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

The pharmaceutical compositions of the present invention can be formulated for pulmonary administration, whether for nasal or buccal inhalation. The unit dosage of the pharmaceutical composition may be conveniently delivered in the form of an aerosol spray from a pressurized pack or a nebulizer, or via a vaporizer. The pharmaceutical compositions may also be delivered as a formulated powder and the powder composition may be inhaled with the aid of an insufflation powder inhaler device. One example of a delivery system for inhalation is a metered dose inhalation (MDI) aerosol, which may be formulated as a dry suspension or wet solution of a pharmaceutical composition of the invention in a suitable propellant, such as a fluorocarbon solvent or a hydrocarbon solvent. Suitable fluorocarbon solvents include HFA-134a (1,1,1,2-tetrafluoroethane), HFA-227ea (1,1,1,2,3,3,3-heptafluoropropane), HFA-152a (1,1-difluoroethane) and combinations thereof. For propellant formulations, the propellant may be present in an amount that is at least 5% by weight, at least 10% by weight, at least 25% by weight, at least 50% by weight at least 75% by weight, or at least 90% by weight, relative to the entire formulation. In some embodiments, the propellant is present in an amount from 80-99.9% by weight, or from 90-99.9% by weight, relative to the entire formulation. The propellant formulation may also include one or more stabilizing excipients, such as ethanol and oleic acid. When ethanol is used, it may be present in an amount from 0.5-10% by weight, from 1-5% by weight, or from 5-10% by weight, relative to the entire formulation. The propellant formulations may further include one or more surfactants, for instance in an amount from 0.1-2.5% by weight, or from 0.2-1.5% by weight, relative to the entire formulation.

The compounds may be in particulate form to enhance delivery to the lung. For example, the compounds may be provided with a particle from 0.1-10 µm, from 0.1-5 µm, from 0.5-2.5 µm, from 1-5 µm, from 2.5-5 µm, or from 1-2.5 µm. In the case of dry powder formulations, the disclosed compounds may be provided in an amount from 1-50% by weight, from 1-50% by weight, from 5-50% by weight, from 1-25% by weight, from 10-25% by weight, from 15-50% by weight, or from 25-50% by weight relative to the total weight of the formulation. The dry powder formulations may further include a powdered matrix material, for example a polyol or carbohydrate, e.g., sorbitol, mannitol, xylitol, glucose, arabinose, lactose, maltose, saccharose, dextrose and mixtures thereof. The compositions may further include a surfactant, for example in an amount from 0.1-10% by weight, from 0.1-5% by weight, 1-10% by weight, from 1-5% by weight, 2.5-10% by weight, or from 2.5-5% by weight. Suitable surfactants include lecithin, phospholipids derivatives such as phosphatic acids, phosphatidyl choline (saturated and unsaturated), phosphatidyl ethanol amine, phosphatidyl glycerol, phosphatidyl serine, phosphatidyl inositol, dioleoylphosphatidylcholine, dimyristoyl phosphatidylcholine, dipalmitoylphosphatidylcholine, distearoyl phosphatidylcholine, diarachidoyl phosphatidylcholine, dibenoyl phosphatidylcholine, ditricosanoyl phosphatidylcholine, dilignoceroylphatidylcholine, dimiristoylphosphatidylethanol-amine, dipalmitoyl-phosphatidylethanoalamine, pipalmitoleoylphasphatidylethanolamine, distearoyl-phosphatidylethanolamine, dimyristoylphosphatidylglycerol, dipalmitoylphosphatidyl glycerol, dipalmitolcoylphosphatidylglycerol, and mixtures thereof.

In addition, any other appropriate route for administration can be employed, for example, but not limited to, intravenous, parenteral, transbuccal, transdermal, transcutaneous, subcutaneous, intranasal, aerosol, or oral administration. Therapeutic formulations may be in the form of liquid solutions or suspensions; for example, for oral administration, formulations may be in the form of tablets or capsules; for intranasal formulations, in the form of powders, nasal drops, or aerosols; for transdermal formulations, in the form of creams or distributed onto patches to be applied to the skin.

Effective amounts of the one compounds disclosed herein in a pharmaceutical formulation will vary depending on the compound being used and the condition or disease being treated, as well as factors such as age of the subject and other medications being taken. Effective dosages will typically be set by an attending physician as is well known in the art. However, the concentration of the compounds delivered to a subject in a unit dose will generally range from about 0.05 mg to about 100 mg, or a value within this range. The combinations can be administered in combinations and/or in combination with one or more other agent (e.g. but not limited to a beta-agonist such as albuterol). In one non-limiting example provided herein, the compounds can be administered with either isoproterenol or chloroquine is additive; thus, under some circumstances, it can be appropriate to administer either (or both) of these agents combination with the compounds disclosed herein to a subject in need thereof.

As used herein, the terms "dose", "dosage", "unit dose", "unit dosage", "effective dose" and related terms refer to physically discrete units that contain a predetermined quantity of active ingredient calculated to produce a desired therapeutic effect (e.g., bronchodilation or relaxation of the airways). These terms are synonymous with the therapeutically effective amounts and amounts sufficient to achieve the stated goals of the methods disclosed herein.

As used herein, the terms "treat", "treating", and "treatment" have their ordinary and customary meanings, and include one or more of, ameliorating a symptom of an obstructive lung disease or condition in a subject, blocking or ameliorating a recurrence of a symptom of an obstructive lung disease or condition in a subject, decreasing in severity and/or frequency a symptom of an obstructive lung disease or condition in a subject. As used herein, "treatment" includes at least partially, and at least temporarily, relieving bronchoconstriction (or bronchospasm) or increasing bronchodilation, so that the patient or subject can breathe more easily. Treatment means ameliorating, blocking, reducing, decreasing or inhibiting by about 1% to about 100% versus a subject to which a pharmaceutical composition has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition has not been administered.

As used herein, the terms "prevent", "preventing", and "prevention" have their ordinary and customary meanings, and include one or more of preventing a symptom of an obstructive lung disease or condition in a subject, blocking a recurrence of a symptom of an obstructive lung disease or condition in a subject, and decreasing in frequency a symptom of an obstructive lung disease or condition in a subject. As used herein, "prevention" includes at least partially, and at least temporarily, blocking bronchoconstriction (or bronchospasm) so that breathing is not inhibited in the patient or subject. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 1, 2, 3, 4, 5, 6, 7, 8, 9, 10, 11, 12, 13, 14, 15, 16, 17, 18, 19, 20, 21, 22, 23, or 24, or more, hours after administration of a pharmaceutical composition.

EXAMPLES

The following examples are for the purpose of illustration of the invention only and are not intended to limit the scope of the present invention in any manner whatsoever.

Figure 2:
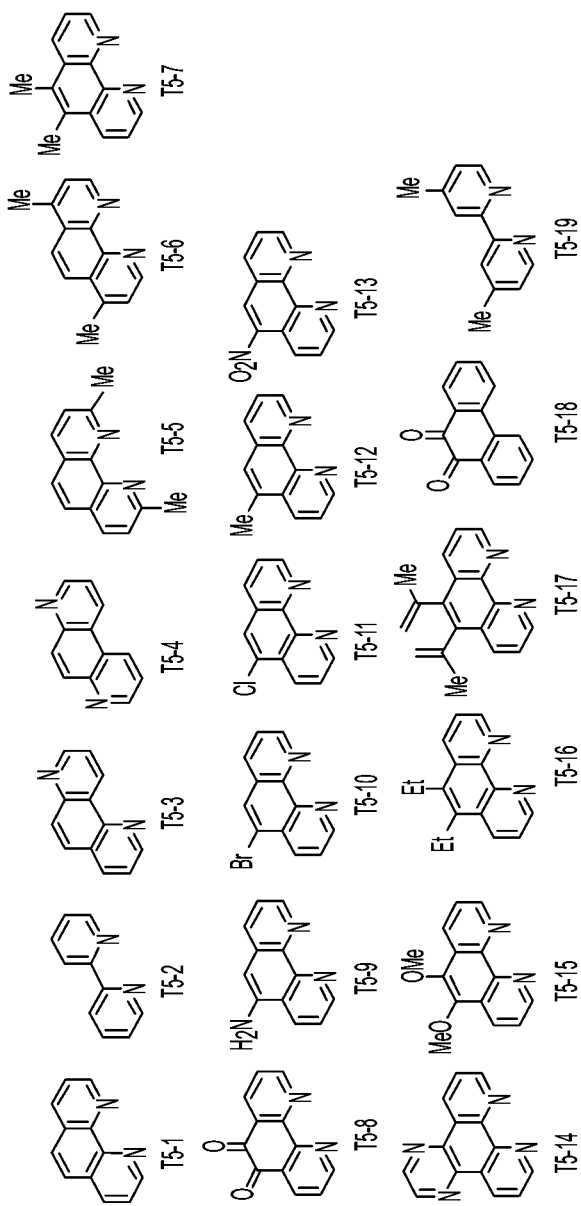
FIG. 2 depicts the chemical structures of compounds screened for $[Ca^{2+}]_i$ stimulation and relaxation in HASM cells.
Figure 3A:
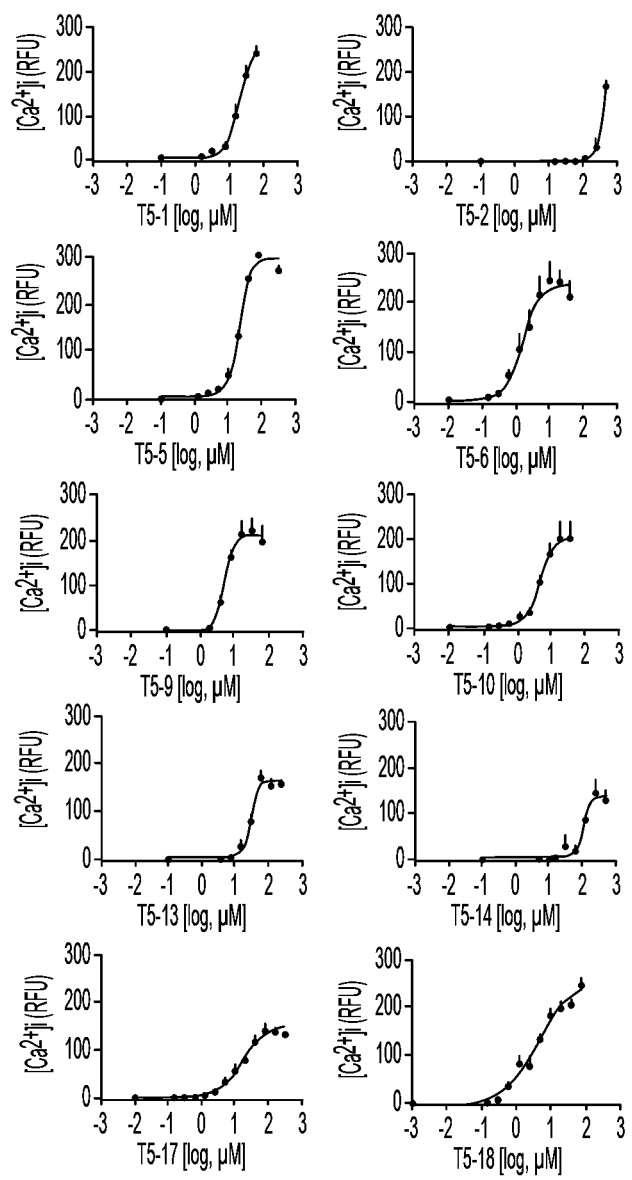
FIG. 3A depicts the Concentration-response curves of compounds screened for stimulation of $[Ca^{2+}]_i$ in D9-HASM cells. Results are mean±SE from 4-8 experiments.
Figure 3B:
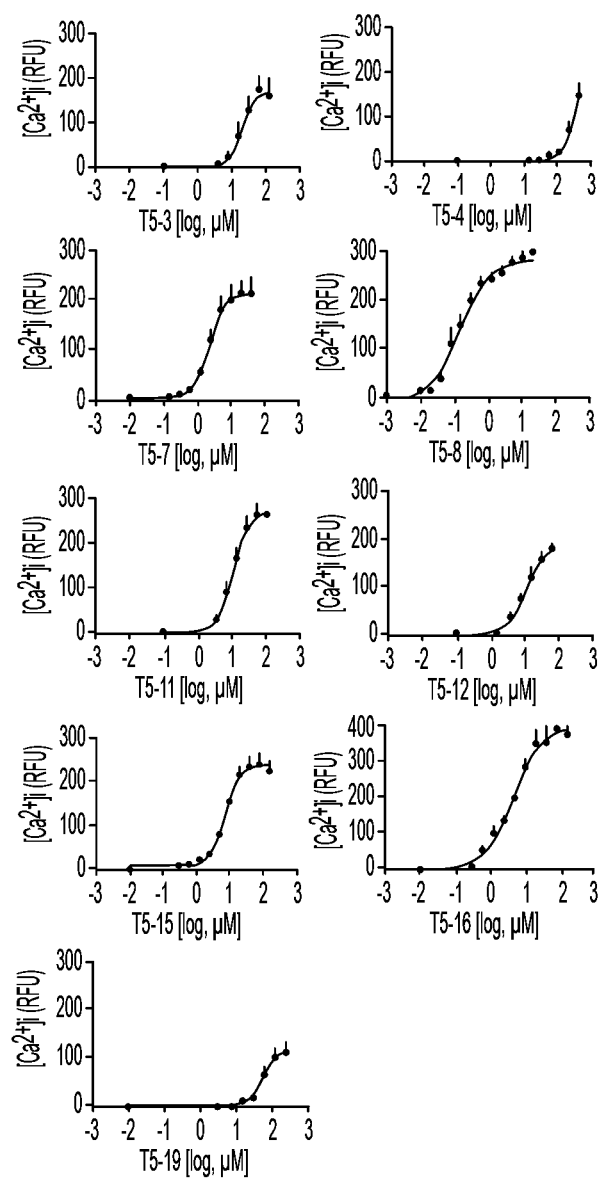
FIG. 3B depicts the Concentration-response curves of compounds screened for stimulation of $[Ca^{2+}]_i$ in D9-HASM cells. Results are mean±SE from 4-8 experiments.
Figure 4A:
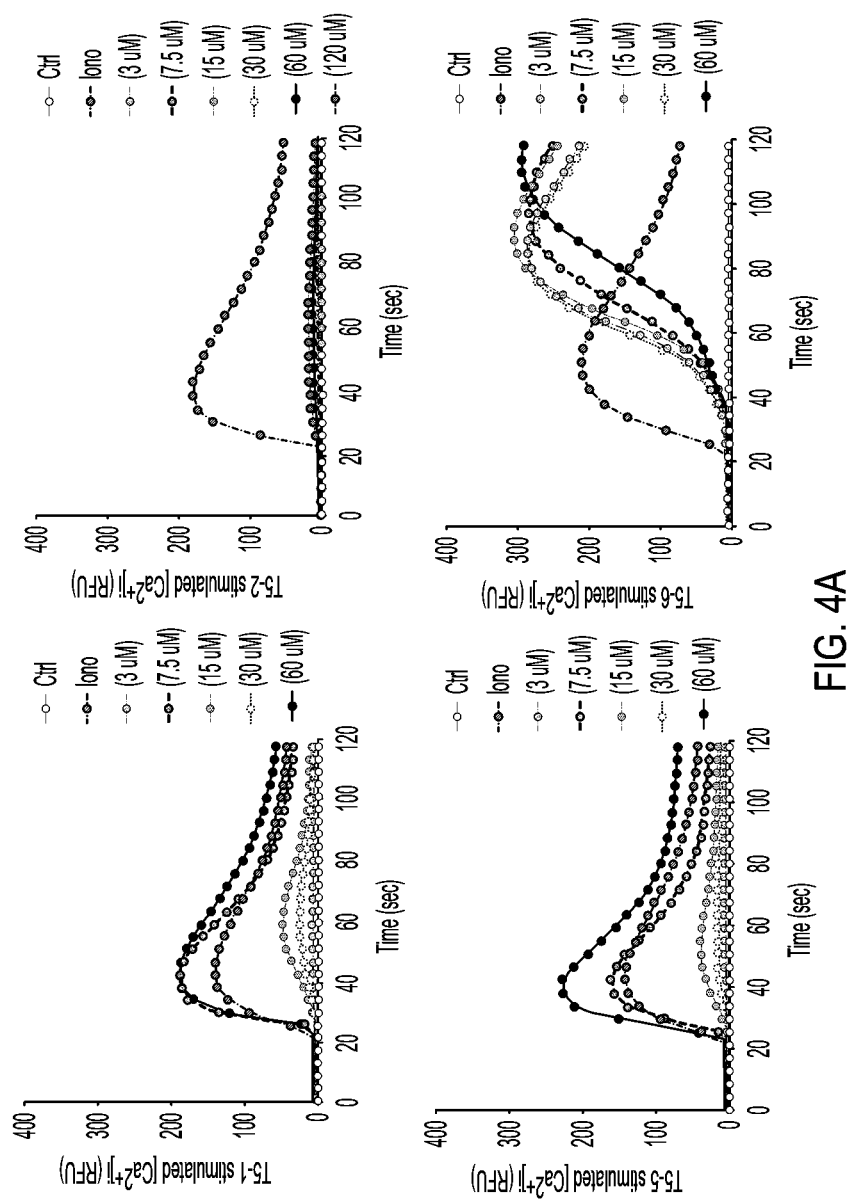
FIG. 4A depicts representative $[Ca^{2+}]i$ responses in D9-HASM cells over 100 seconds after exposure to the indicated compounds.
Figure 4B:
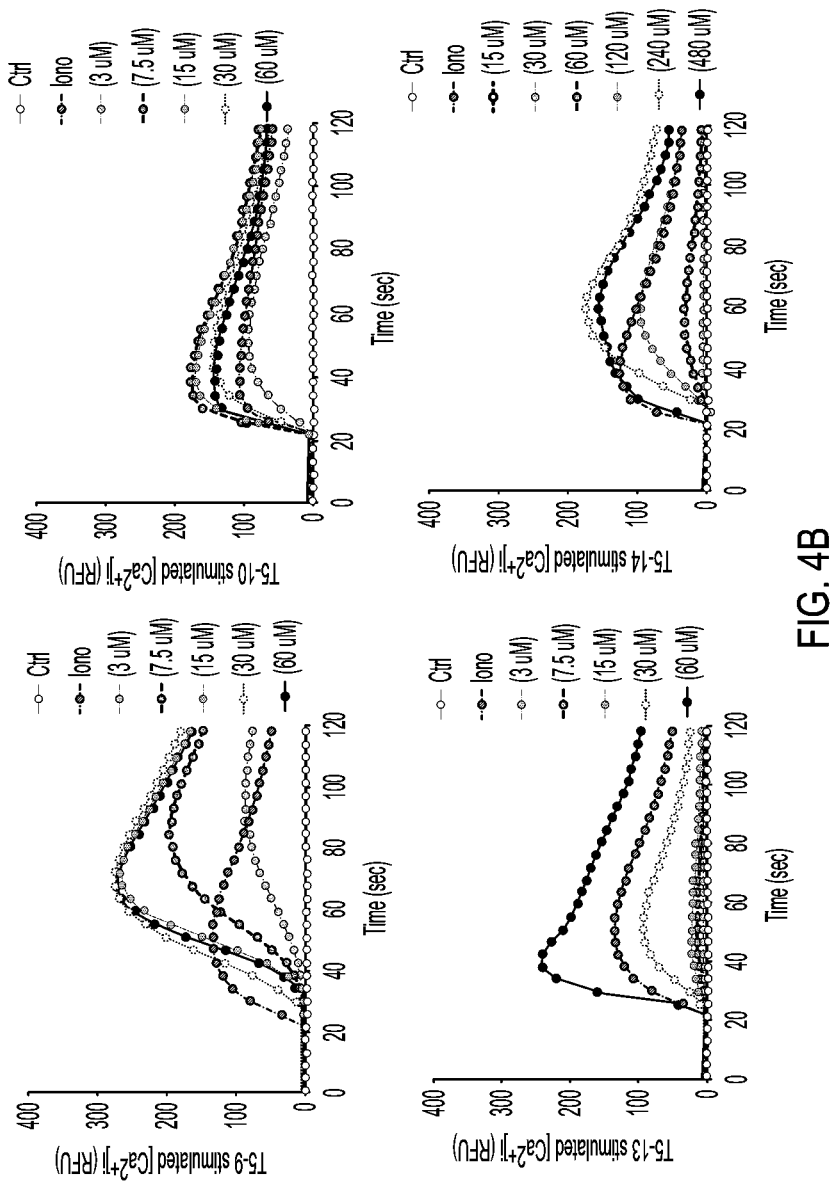
FIG. 4B depicts representative $[Ca^{2+}]i$ responses in D9-HASM cells over 100 seconds after exposure to the indicated compounds.
Figure 4C:
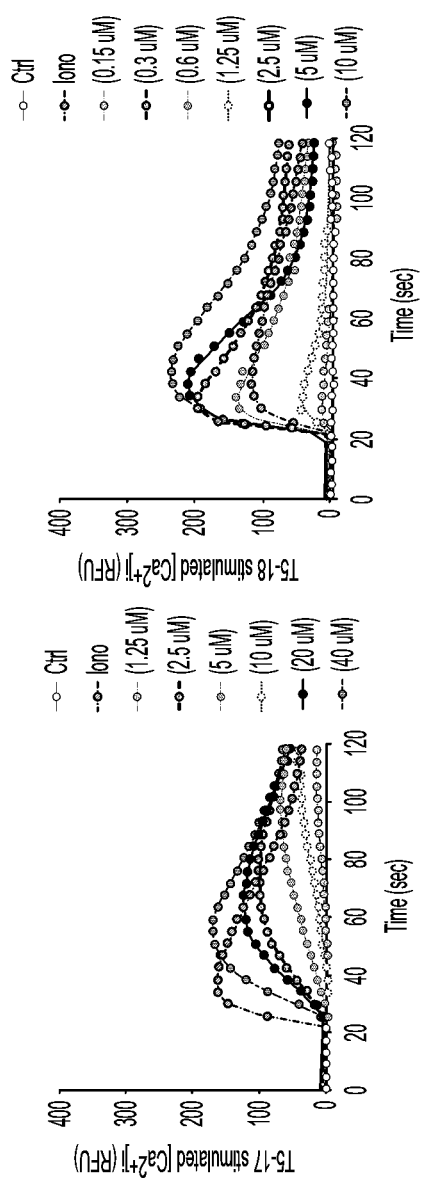
FIG. 4C depicts representative $[Ca^{2+}]i$ responses in D9-HASM cells over 100 seconds after exposure to the indicated compounds.
Figure 4D:
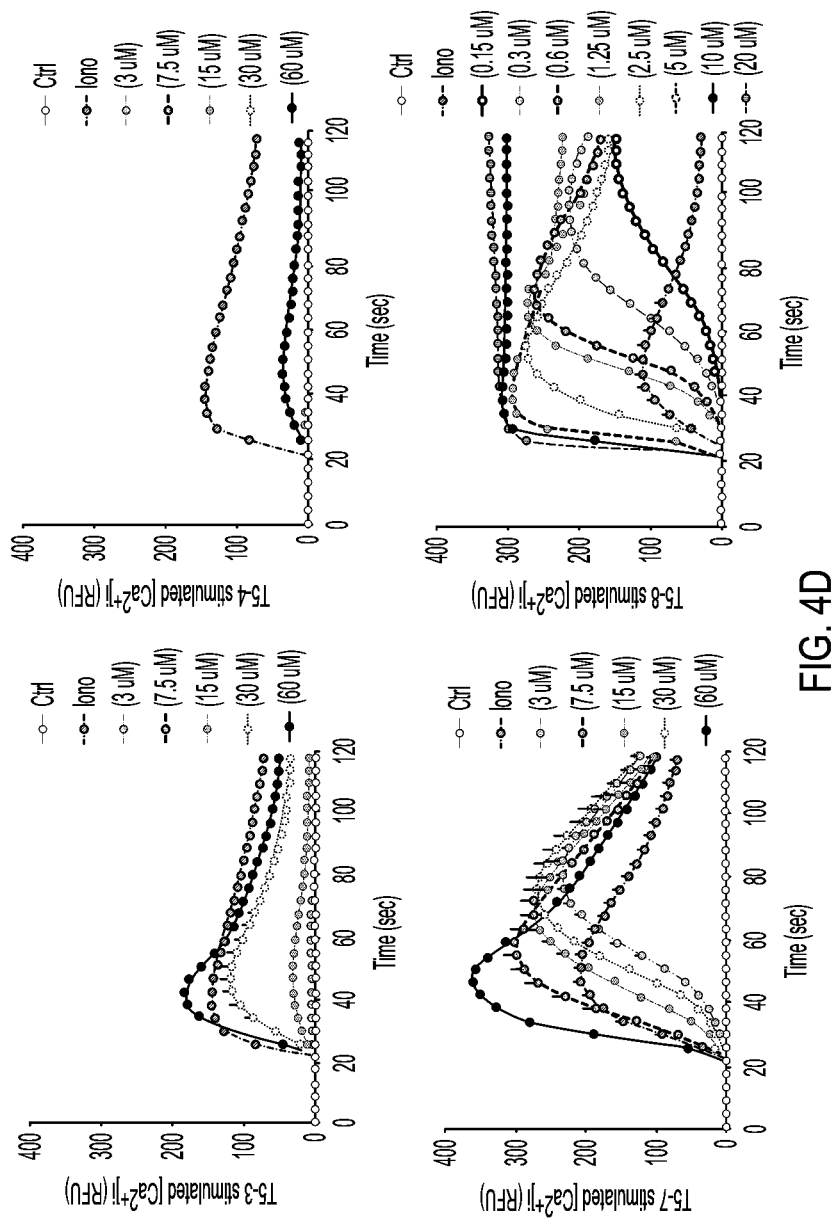
FIG. 4D depicts representative $[Ca^{2+}]i$ responses in D9-HASM cells over 100 seconds after exposure to the indicated compounds.
Figure 4E:
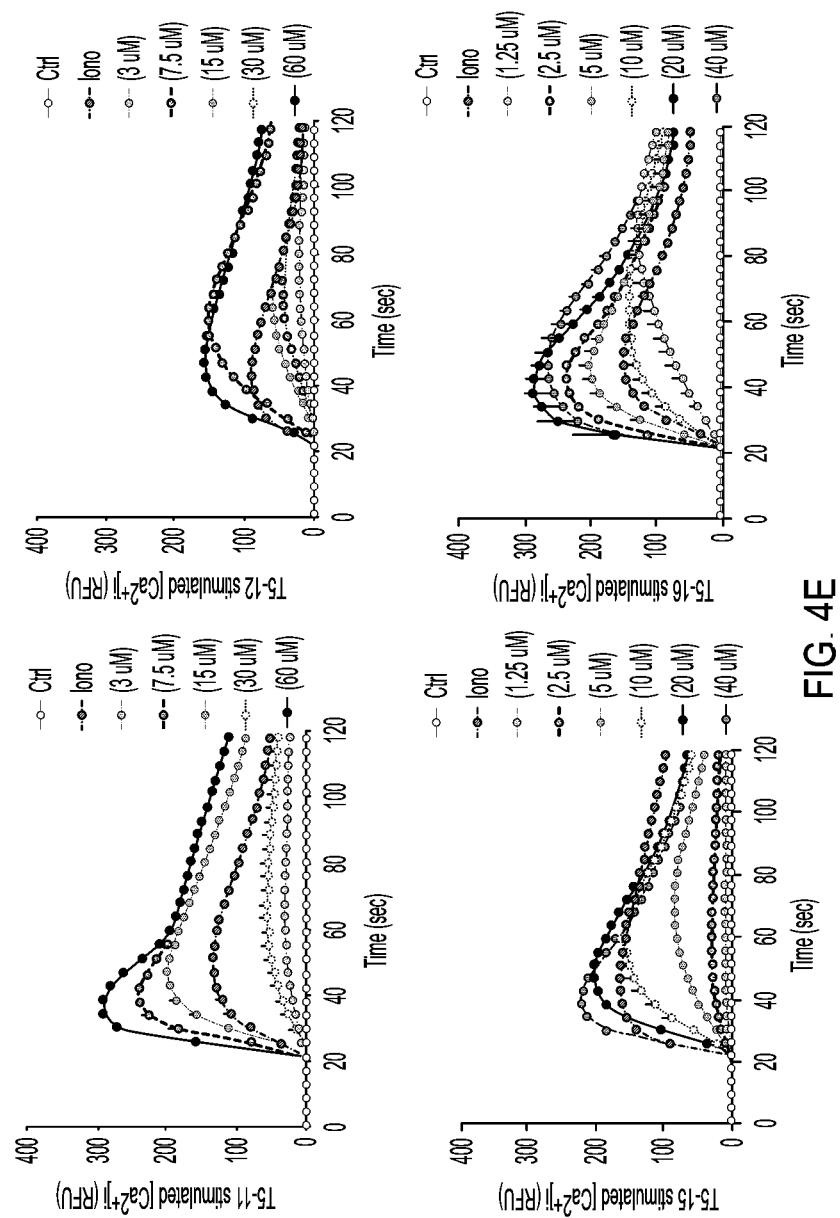
FIG. 4E depicts representative $[Ca^{2+}]i$ responses in D9-HASM cells over 100 seconds after exposure to the indicated compounds.
Figure 4F:
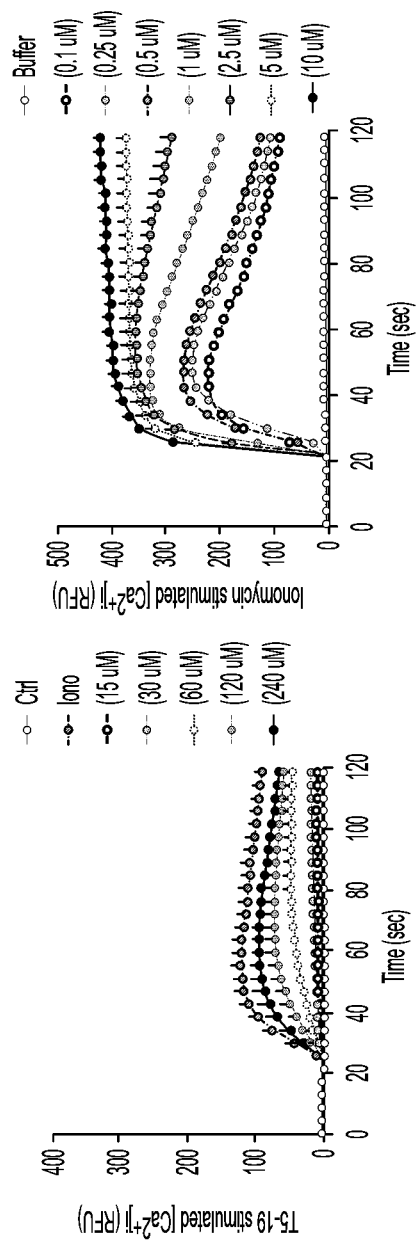
FIG. 4F depicts representative $[Ca^{2+}]i$ responses in D9-HASM cells over 100 seconds after exposure to the indicated compounds.
Figure 5:
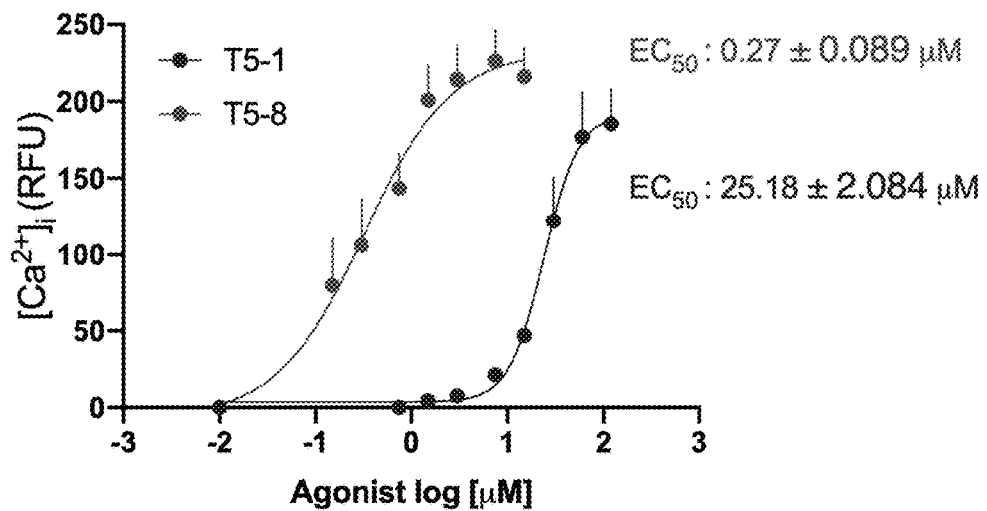
FIG. 5 depicts $[Ca^{2+}]_i$ responses in primary HASM cells with T5-1 and T5-8. Cultured primary HASM cells at passages 5-7 derived from a non-asthmatic lung were exposed to the indicated concentrations of the agonists. Results are from 4 independent experiments. *, EC50 P<0.01 vs T5-1.

Cultured $D_9$ telomerase reverse transcriptase immortalized HASM (D9-HASM) cells were utilized for the $[Ca^{2+}]_i$ screening assays. Cells were seeded onto 96 well plates and loaded with Fluo-4 direct. The $[Ca^{2+}]_i$ responses to multiple concentrations of potential agonists were determined as a measure of receptor activation. Control cells were exposed to the non-specific ionophore ionomycin at 2.0 µM (a maximal effective concentration, FIG. 4). Results from TAS2R agonist studies were normalized to the ionomycin response in order to compare the maximal responses (Rmax) between agonists. The concentration-response data were fit to a four component logistic regression model (sigmoid curve) using iterative non-linear regression methods to determine the $EC_{50}$ and Rmax. The structures of the previously identified agonist termed T5-1, and 18 derivatives (denoted as T5-2 through T5-19) are shown in FIG. 2. Representative $[Ca^{2+}]_i$ responses to these compounds are shown in FIG. 4, and mean results from multiple concentration-response experiments are shown in FIG. 3. Table 1 summarizes the results in terms of potency ($EC_{50}$) and efficacy (Rmax), with statistical comparisons to T5-1.

Figure 6:
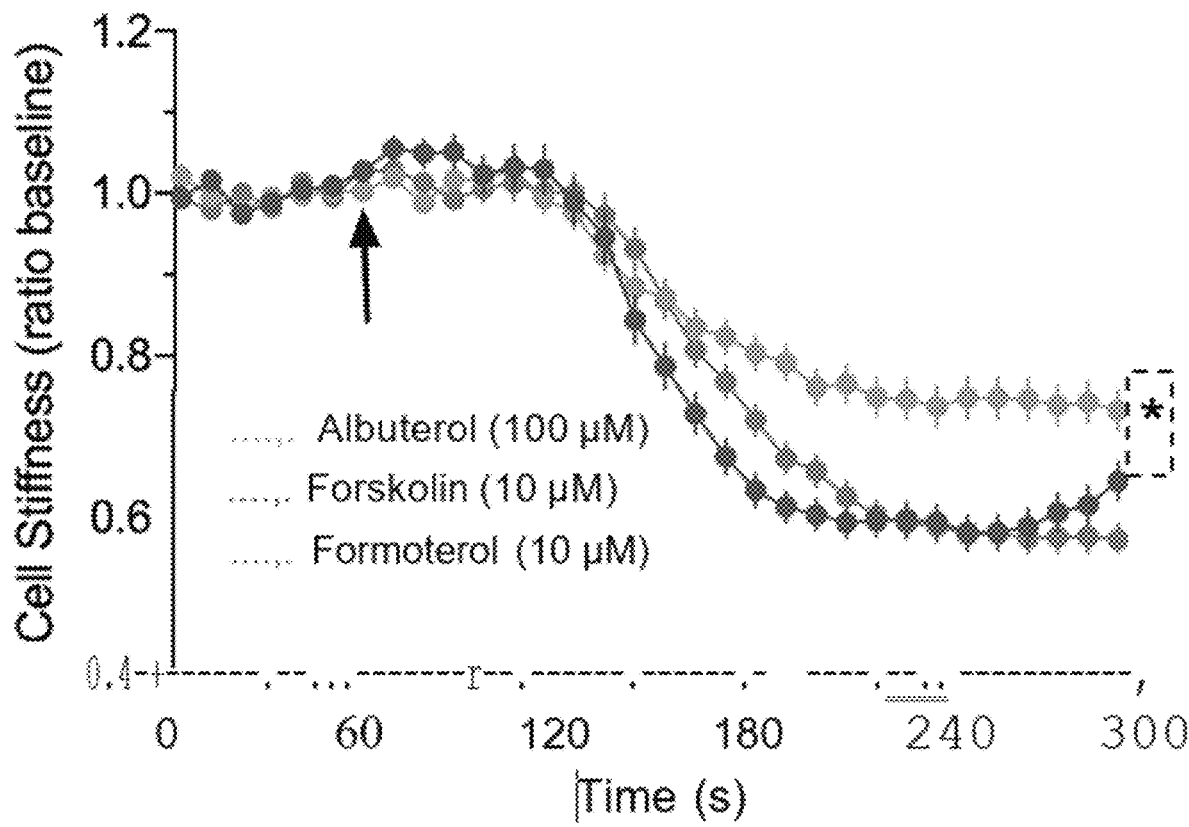
FIG. 6 depicts HASM relaxation responses to non-TAS2R5 agonists measured by MTC. Cells were exposed to the beta-agonists albuterol (partial agonist), formoterol (full agonist), and the direct activator of adenylyl cyclase, forskolin. Results are from 200-300 measurements per condition. *, peak maximal response less than formoterol, P<0.01.
Figure 7:
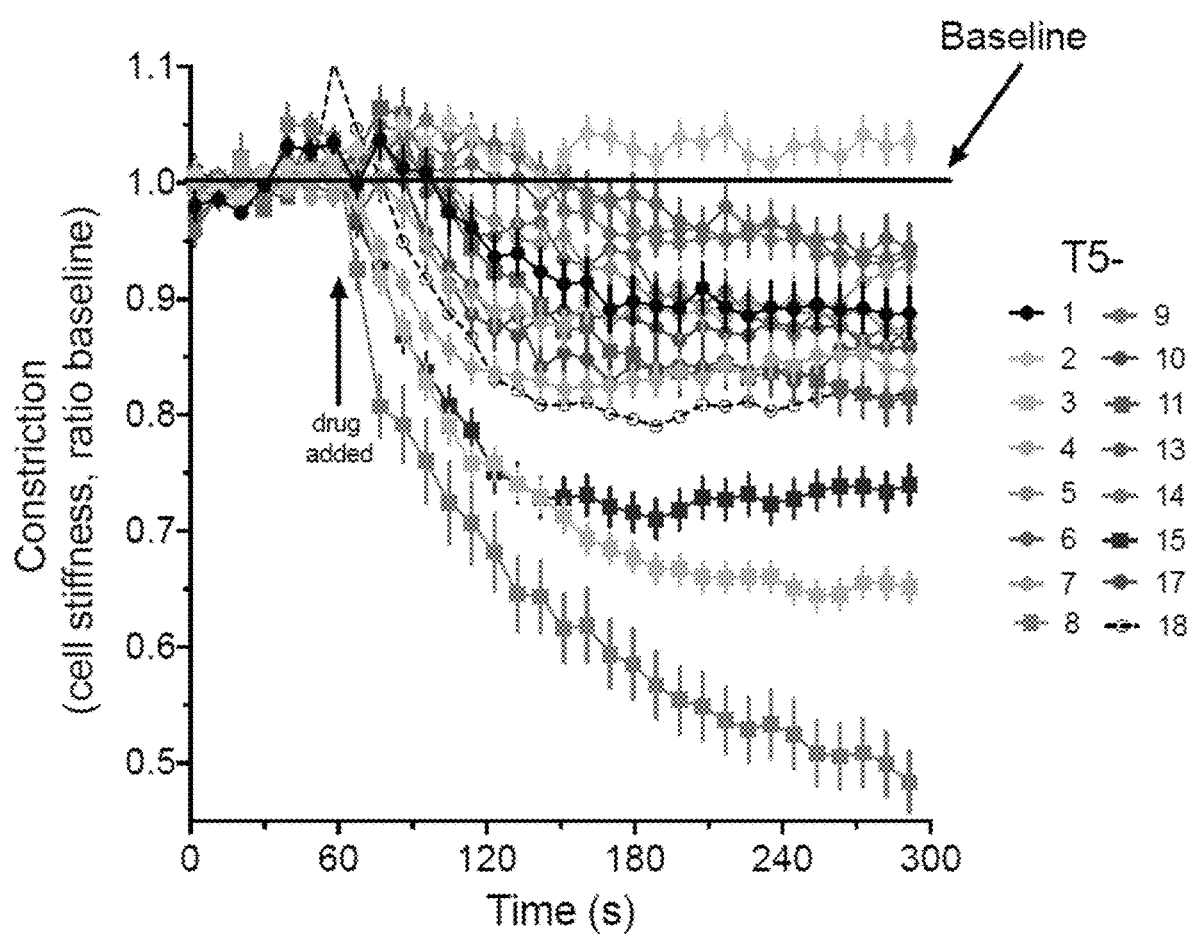
FIG. 7 depicts HASM cell relaxation responses to selected compounds. Compounds were studied at a concentration of 500 µM and were added to the culture media at the 60 second time point (arrow). Results are from measurements of 200-400 cells per compound. *, P<0.01 vs the T5-1 reference response. As can be seen, compound 8 gave the greatest degree of relaxation, followed by 3, then 15, then 18 and 11.
Figure 8:
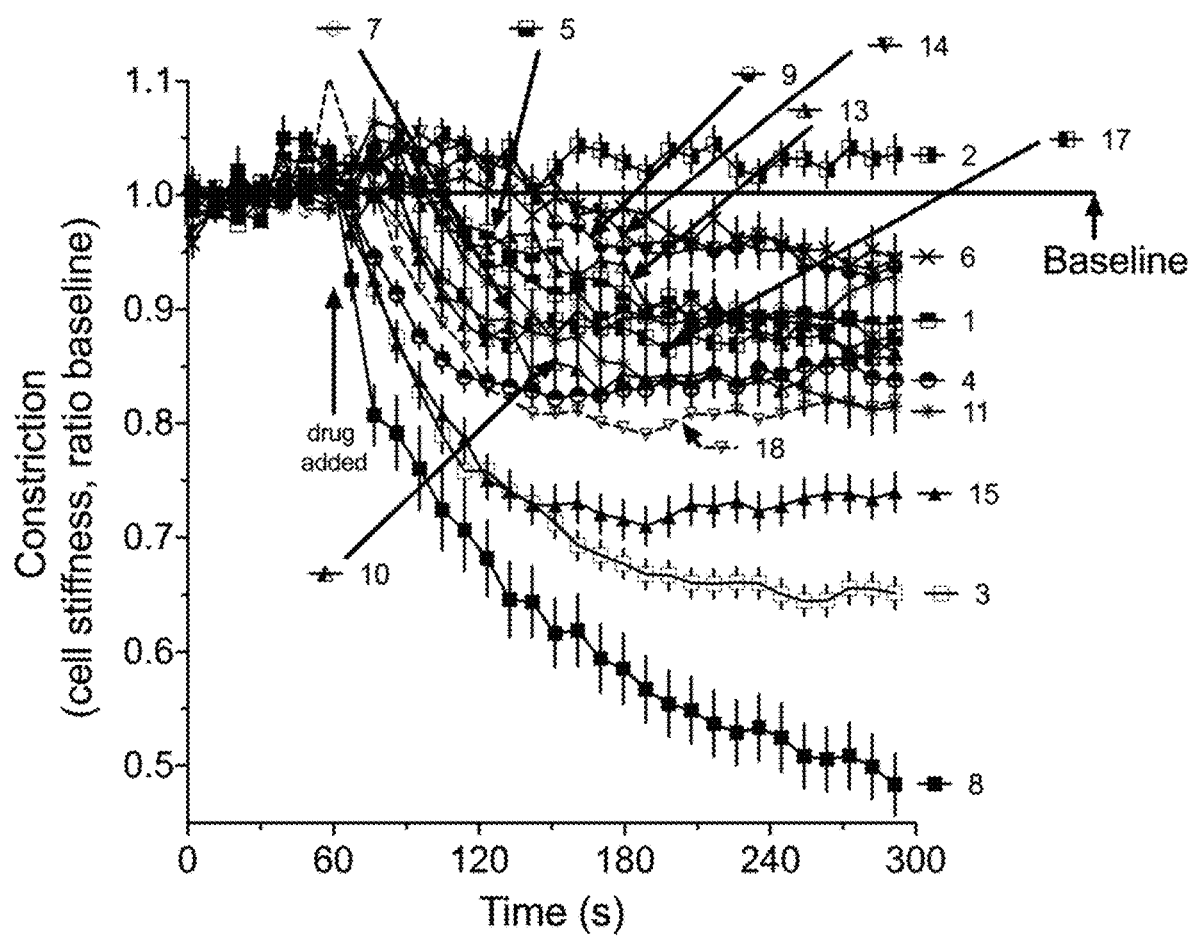
FIG. 8 depicts the same information as FIG. 7, but with additional identifying information for each data stream.

To correlate the $[Ca^{2+}]_i$ responses of the compounds to relevant physiologic function, we turned to measurements of single-cell mechanics in HASM cells using magnetic twisting cytometry (MTC) as previously described. Here, cultured primary HASM cells at passages 5-7 derived from a non-asthmatic donor lung were utilized. The decrease in cell stiffness evoked by a compound on the ferrimagnetically tagged HASM cells, twisted by a magnetic field, has been found to correlate with clinical airway relaxation. For these studies a single concentration of all agonists was utilized, recognizing that the 3 log differences in $EC_{50}$ values observed with the compounds would yield a range of relaxation responses consistent with the structure-activity relationships established in the $[Ca^{2+}]_i$ assays, with some caveats (see below). Positive controls (FIG. 6) included the β-agonists albuterol (partial agonist), formoterol (full agonist) and forskolin, which increases cAMP by direct activation of adenylyl cyclase. The results from these studies are shown in FIG. 4 and Table 1.

TABLE 1

$[Ca^{2+}]_i$ stimulation and smooth muscle relaxation responses of HASM cells to the indicated compounds

| Agonist | Abbreviation | $EC_{50}$ (µM) | Rmax (% ionomycin) | Relaxation (% basal) |
|---|---|---|---|---|
| 1,10-Phenanthroline | T5-1 | 29.7 ± 5.57 | 149 ± 10.23 | 10.8 ± 2.17[#] |
| 2,2'-Bipyridine | T5-2 | N/A | 16.4 ± 4.48 | −3.2 ± 1.67 |
| 1,7-Phenanthroline | T5-3 | 24.9 ± 4.58 | 121 ± 16.7 | 34.8 ± 1.36[#] |
| 4,7-Phenanthroline | T5-4 | N/A | 15.4 ± 3.37* | 15.3 ± 1.48[#] |
| 2,9-Dimethyl-1,10-phenanthroline | T5-5 | 33.3 ± 6.40 | 143 ± 13.1 | 12.0 ± 1.47[#] |
| 4,7-Dimethyl-1,10-phenanthroline | T5-6 | 1.39 ± 0.19* | 147 ± 16.7 | 5.3 ± 1.95[#] |
| 5,6-Dimethyl-1,10-phenanthroline | T5-7 | 2.05 ± 0.20* | 163 ± 36.4 | 9.0 ± 2.19[#] |
| 1,10-Phenanthroline-5,6-dione | T5-8 | 0.12 ± 0.05* | 199 ± 20.2* | 50.2 ± 2.79[#] |
| 1,10-Phenanthrolin-5-amine | T5-9 | 4.60 ± 0.42* | 176 ± 14.2 | 7.2 ± 1.95[#] |
| 5-Bromo-1,10-phenanthroline | T5-10 | 4.35 ± 0.71* | 182 ± 25.7 | 14.4 ± 1.93[#] |
| 5-Chrolo-1,10-phenanthroline | T5-11 | 11.1 ± 2.00 | 183 ± 7.3 | 18.0 ± 2.13[#] |

TABLE 1-continued

[Ca$^{2+}$]$_i$ stimulation and smooth muscle relaxation responses of HASM cells to the indicated compounds

| Agonist | Abbreviation | EC$_{50}$ (μM) | Rmax (% ionomycin) | Relaxation (% basal) |
|---|---|---|---|---|
| 5-Methyl-1,10-phenanthroline | T5-12 | 12.1 ± 1.99 | 181 ± 24.6 | ND |
| 5-Nitro-1,10-phenanthroline | T5-13 | 36.0 ± 3.85 | 134 ± 11.9 | 12.8 ± 2.00# |
| Pyrazino[2,3-f][1,10]phenanthroline | T5-14 | 146.6 ± 2.26* | 34.5 ± 15.1* | 6.1 ± 1.67# |
| 5,6-Dimethoxy-1,10-phenanthroline | T5-15 | 7.48 ± 0.78* | 127 ± 16.1 | 26.7 ± 1.65# |
| 5,6-Diethyl-1,10-phenanthroline | T5-16 | 4.05 ± 0.80* | 183 ± 14.7 | ND |
| 5,6-di(prop-1-en-2yl)-1,10-phenanthroline | T5-17 | 25.5 ± 7.06 | 113 ± 19.0 | 13.5 ± 2.59# |
| 9,10-Phenanthrenequinone | T5-18 | 5.08 ± 1.37* | 153 ± 5.2 | 20.0 ± 2.00# |
| 4,4'-Dimethyl-2,2'-dipyridyl | T5-19 | 60.6 ± 9.13* | 58.9 ± 2.95* | ND |

*EC$_{50}$ or Rmax different than T5-1, P < 0.05([Ca$^{2+}$]$_i$ assays).
Relaxation greater than baseline, P < 0.05(MTC assays).
N/A, not applicable because of lack of curve fit
ND, The experiment was not done The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for treating an obstructive lung disease in a patient in need thereof, comprising administering to the patient a compound having the formula:

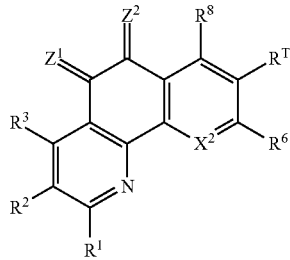

or a pharmaceutically acceptable salt thereof, wherein $Z^1$ is O, S, or NR$^a$; wherein R$^a$ is H, C$_{1-8}$alkyl, or C$_{1-8}$alkoxy;

$Z^2$ is O, S, or NR$^b$; wherein R$^b$ is H, C$_{1-8}$alkyl, or C$_{1-8}$alkoxy;

R$^1$ is selected from R$^a$, OR$^a$, N(R$^a$)$_2$, F, Cl, Br, I, NO$_2$, CN, wherein R$^a$ is in each case selected from H, C$_{1-8}$alkyl, C$_{2-8}$alkenyl; C$_{2-8}$alkynyl;

R$^2$ is selected from R$^b$, OR$^b$, N(R$^b$)$_2$, F, Cl, Br, I, NO$_2$, CN, wherein R$^b$ is in each case selected from H, C$_{1-8}$alkyl, C$_{2-8}$alkenyl; C$_{2-8}$alkynyl;

R$^3$ is selected from R$^c$, OR$^c$, N(R$^c$)$_2$, F, Cl, Br, I, NO$_2$, CN, wherein R$^c$ is in each case selected from H, C$_{1-8}$alkyl, C$_{2-8}$alkenyl; C$_{2-8}$alkynyl;

wherein any two or more of R$^1$, R$^2$, and R$^3$ may together form a ring; and X$^2$ is N;

R$^6$ is selected from R$^d$, OR$^d$, N(R$^d$)$_2$, F, Cl, Br, I, NO$_2$, CN, wherein R$^d$ is in each case selected from H, C$_{1-8}$alkyl, C$_{2-8}$alkenyl; C$_{2-8}$alkynyl;

R$^7$ is selected from R$^e$, OR$^e$, N(R$^e$)$_2$, F, Cl, Br, I, NO$_2$, CN, wherein R$^e$ is in each case selected from H, C$_{1-8}$alkyl, C$_{2-8}$alkenyl; C$_{2-8}$alkynyl;

R$^8$ is selected from R$^f$, OR$^f$, N(R$^f$)$_2$, F, Cl, Br, I, NO$_2$, CN, wherein R$^f$ is in each case selected from H, C$_{1-8}$alkyl, C$_{2-8}$alkenyl; C$_{2-8}$alkynyl;

wherein any two or more of R$^6$, R$^7$, and R$^8$ may together form a ring; and wherein R$^8$ may form a ring with R$^b$, wherein the obstructive lung disease is asthma, chronic obstructive pulmonary disease, emphysema, bronchitis, cystic fibrosis, bronchiectasis, bronchiolitis, or allergic bronchopulmonary aspergillosis.

2. The method according to claim 1, wherein $Z^1$ and $Z^2$ are both O.

3. The method according to claim 1, wherein $R^3$ and $R^8$ are each H.

4. The method according to claim 1, wherein $R^2$ and $R^7$ are each H.

5. The method according to claim 1, wherein $R^1$ and $R^6$ are each H.

6. The method according to claim 1, wherein $R^1$, $R^2$, $R^3$, $R^6$, $R^7$, and $R^8$ are each H.

7. The method according to claim 2, wherein $R^1$, $R^2$, $R^3$, $R^6$, $R^7$, and $R^8$ are each H.

8. The method according to claim 1, wherein the obstructive lung disease is asthma.

9. The method according to claim 1, wherein the obstructive lung disease is chronic obstructive pulmonary disease.

10. The method according to claim 1, wherein the obstructive lung disease is emphysema.

11. The method according to claim 1, wherein the obstructive lung disease is bronchitis.

12. The method according to claim 1, wherein the obstructive lung disease is cystic fibrosis.

13. The method according to claim 1, wherein the obstructive lung disease is bronchiectasis.

14. The method according to claim 1, wherein the obstructive lung disease is bronchiolitis.

15. The method according to claim 1, wherein the obstructive lung disease is allergic bronchopulmonary aspergillosis.

16. The method according to claim 1, wherein the compound is administered by inhalation.

* * * * *